(12) United States Patent
Roy et al.

(10) Patent No.: US 11,090,024 B2
(45) Date of Patent: Aug. 17, 2021

(54) BIOPSY AND SONOGRAPHY METHOD AND APPARATUS FOR ASSESSING BODILY CAVITIES

(71) Applicant: CrossBay Medical, Inc., San Diego, CA (US)

(72) Inventors: Kelly H. Roy, Phoenix, AZ (US); Steven R. Bacich, Half Moon Bay, CA (US); Piush Vidyarthi, San Rafael, CA (US); Donnell W. Gurskis, Belmont, CA (US); Cristiano Danilo Maria Fontana, Assago (IT)

(73) Assignee: CrossBay Medical, Inc., San Diego, CA (US)

(*) Notice: Subject to any disclaimer, the term of this patent is extended or adjusted under 35 U.S.C. 154(b) by 178 days.

(21) Appl. No.: 16/242,900

(22) Filed: Jan. 8, 2019

(65) Prior Publication Data
US 2019/0142370 A1 May 16, 2019

Related U.S. Application Data

(60) Continuation of application No. 14/472,200, filed on Aug. 28, 2014, now abandoned, which is a division of application No. 13/830,202, filed on Mar. 14, 2013, now abandoned.

(60) Provisional application No. 61/723,114, filed on Nov. 6, 2012.

(51) Int. Cl.
*A61B 8/12* (2006.01)
*A61B 10/02* (2006.01)
*A61B 8/00* (2006.01)

(52) U.S. Cl.
CPC .............. *A61B 8/12* (2013.01); *A61B 8/42* (2013.01); *A61B 8/4416* (2013.01); *A61B 10/0291* (2013.01); *A61B 10/0283* (2013.01)

(58) Field of Classification Search
CPC .......... A61B 8/12; A61B 8/42; A61B 10/0291
See application file for complete search history.

(56) References Cited

U.S. PATENT DOCUMENTS

| | | |
|---|---|---|
| 2,299,492 A | 10/1942 | Pfauser |
| 4,271,839 A | 6/1981 | Fogarty et al. |
| 4,742,829 A | 5/1988 | Law et al. |
| 5,879,289 A | 3/1999 | Yarush et al. |
| 6,669,643 B1 | 12/2003 | Dubinsky |
| 7,041,084 B2 | 5/2006 | Fojtik |

(Continued)

FOREIGN PATENT DOCUMENTS

| | | |
|---|---|---|
| JP | H0859504 | 4/1996 |
| WO | WO 2014/074522 | 5/2014 |

OTHER PUBLICATIONS

"Saline-Infusion Sonography Endometrial Biopsy in Diagnosing Endometrial Pathology" by E. Moschos et al. Obstetrics & Gynecology. vol. 113, No. 4, pp. 881-887, Apr. 2009.

*Primary Examiner* — Jason M Ip
(74) *Attorney, Agent, or Firm* — Levine Bagade Han LLP (57) ABSTRACT

Apparatuses and methods for performing a procedure on a uterine cavity of a patient are disclosed. The methods can include visualizing the uterine cavity, biopsying a tissue with a biopsy device, and ejecting fluid from the biopsying device into the uterine cavity. The apparatuses can have a sealable acorn tip, a handle, a repositioning clip, a distal indicia, a proximal indicia, and a fluid reservoir. The biopsying device can be configured to biopsy and eject fluid under the control of a single hand of a user of the device.

18 Claims, 11 Drawing Sheets

(56) References Cited

U.S. PATENT DOCUMENTS

| | | |
|---|---|---|
| 8,157,745 B2 | 4/2012 | Schoot |
| 8,221,322 B2 | 7/2012 | Wang et al. |
| 2007/0135796 A1 | 6/2007 | Gorodeski |
| 2008/0045924 A1 | 2/2008 | Cox et al. |
| 2008/0097470 A1 | 4/2008 | Gruber et al. |
| 2009/0156996 A1 | 6/2009 | Milsom et al. |
| 2014/0128732 A1 | 5/2014 | Roy et al. |
| 2014/0371597 A1 | 12/2014 | Roy et al. |
| 2018/0235660 A1 | 8/2018 | Bacich |

FIG. 1
NOT INVENTION

FIG. 2b  NOT INVENTION

FIG. 2c

NOT INVENTION

BIOPSY AND SONOGRAPHY METHOD AND APPARATUS FOR ASSESSING BODILY CAVITIES

CROSS-REFERENCE TO RELATED APPLICATIONS

This application is a continuation of U.S. patent application Ser. No. 14/472,200, filed Aug. 28, 2014, which is a divisional application of U.S. patent application Ser. No. 13/830,202, filed Mar. 14, 2013, now abandoned, which claims the benefit of U.S. Provisional Application No. 61/723,114, filed 6 Nov. 2012, all of which are incorporated by reference herein in their entireties.

FIELD OF THE DISCLOSURE

The present disclosure generally relates to procedures for assessing bodily cavities such as the uterine cavity. Such procedures utilize ultrasonography and the removal of bodily tissue for further pathological analysis. Methods for the assessment of the uterine cavity and endometrial lining of the uterus can be performed by the devices disclosed herein. Methods of the delivery of drugs, agents, and therapeutic devices in targeted locations of the uterus are disclosed herein. Methods for performing an endometrial biopsy and saline infusion sonography (SIS) in a simplified fashion that can enable the physician to perform these procedures while simultaneously operating ultrasonographic probes are disclosed.

BACKGROUND

In gynecological practice, it is standard for women to undergo procedures to assess their uterine cavities and the endometrial tissue, in particular for woman suffering from abnormal bleeding, infertility, suspected cancer, sexually transmitted diseases, pelvic pain, and other maladies of the reproductive tract. These procedures include making an assessment of the uterine cavity with or without saline infusion, assessing the patency of the fallopian tubes, determining the thickness of endometrial lining as per the time of the woman's cycle, examining for uterine abnormalities such as polyps, adhesions, and fibroids within the cavity or wall of the uterus, and performing an biopsy of the uterine lining. As part of the work up, these standard procedures typically are performed in an office setting or small suite without the use of anesthesia for the patient. Since these procedures are typical in the gynecological work up of a patient, a gynecologist could be expected to perform many assessments of the uterine cavity during the course of patient consultations and visits.

Specifically during a uterine cavity assessment, the gynecologist will access the cervix through the vagina by utilizing a speculum. The gynecologist may or may not use a tenaculum to stabilize or straighten the cervical canal depending upon the anatomy and physician preference. For greater patient comfort, the gynecologist seeks to reduce the amount of materials that enter the patient's vagina as well as minimize the number of times different devices need to be inserted within the patient. Patient comfort is further enhanced by a reduced procedural time and due to capitated fee structures and scheduling constraints, the gynecologist also is incentivized to reduce procedural time yet obtaining a proper and efficient diagnosis is paramount.

Using either a vaginal or abdominal ultrasonographic probe, a general assessment of the uterus and surrounding organs can be performed. In an effort to simplify the assessment of the uterine cavity, gynecologists have incorporated the use of saline infusion to distend the cavity and provide further contrast for the detection of uterine cavity abnormalities. The continued injection of saline with or without the use of Doppler ultrasound can provide further information on fallopian tube patency if a spill or free flow of saline in the peritoneal space can be visualized by ultrasound. In some cases the saline can be enhanced for ultrasonography if bubbles or foams are incorporated into the saline fluid. In an effort for further echogenicity, the saline can be replaced by gels that are known to have higher contrast for ultrasonographic detection.

To perform these infusions, gynecologists have employed a variety of catheter tools and many of these devices are indicated for other procedures. For instance, it is standard practice for physicians to use insemination catheters for the infusion of saline into the uterine cavity since these devices are small in diameter or profile, do not require cervical dilation, and they are readily available in the gynecologist's practice. These insemination catheters are typically characterized as single lumen catheters with a smooth distal end opening, flexible shaft, indicia for uterine depth markings in centimeter increments, and a proximal luer connector or coupling for connecting a syringe or fluid source. These simple catheters have no ability to improve the distension of the uterine cavity during infusion and in a majority of cases, especially in multi-parous women, a significant amount of the fluid will escape through the cervical canal.

Other catheters have been developed that improve the infusion of saline through the incorporation of means for blocking or sealing the cervical canal. These catheters also have applications for the fluoroscopic or x-ray assessment of the uterine cavity in a procedure known as hysterosalpingography whereby contrast agents and fluids are injected into the uterine cavity and fallopian tubes for assessment for radiographic techniques. In one form, these catheters have balloons on their distal ends which seal the cervical canal within the lower uterine segment. Following insertion in to the uterine cavity, these distal balloons are inflated and pulled back proximally to allow for the balloon to engage and seal within the lower uterus at the upper endocervical canal. Once pulled into and pressed into the endocervix, the balloon provides a seal for the distension of the uterine cavity. These distal balloons can obscure the lower uterine cavity region from ultrasonographic analysis.

Other catheters have acorn or bulbous tips near their distal end. The purpose of these acorn tips is to occlude the exocervix and thereby maintain pressure or distension in the uterine cavity. In practice the gynecologist presses the acorn tip into and against the exocervix to occlude the cervical opening to improve uterine distension. These acorn tips have come in a variety of shapes and sizes. Typically they are not efficient in providing an adequate seal in most women since the exocervix in women can be highly irregular. Some systems have utilized a tenaculum to provide a compressive force to help stabilize and enforce the pressure of the acorn tip against the exocervix. In practice this combination can be uncomfortable for the patient, especially during the manual injection of fluids or saline into the uterine cavity.

During the gynecological assessment of the uterine cavity, it is desirable to obtain a portion of tissue for pathological analysis. Some devices incorporate the use of vacuum at the distal tip (e.g., PIPELLE® manufactured by Cooper Surgical, Inc. of Trumbull, Conn.). These devices may utilize an inner mandrel that is withdrawn proximally by the physician to create a vacuum force. The vacuum force draws fluid and tissue into the distal opening of the catheter within the uterus. Once removed from the uterine cavity, the distal catheter is placed into a specimen container and the inner mandrel is advanced to expel the contents collected in the distal end into the specimen container.

Another biopsy device utilizes a brush within the inner catheter that is advanced from the distal end of the catheter which is placed within the uterine cavity. The brush (e.g., TAO BRUSH™ manufactured by Cook Medical, Inc of Bloomington, Ind.) is advanced from the distal end of the catheter. The brush is typically rotated in situ to increase the amount of contact with the tissue in the uterine cavity. After several rotations the brush is withdrawn back into the distal end of the catheter and the entire device is removed from the uterus and body of the patient. Once removed, the inner brush is advanced beyond the distal end of the catheter within a specimen container partially filled with fluid or saline. The brush is agitated within the fluid so that tissue on the brush can be released into the fluid so that the specimen container can be processed by the pathologist.

Both of these biopsy devices typically collect tissue without visualization and the devices provide no means for determining their location with the use or ultrasound or radiographic techniques. Thereby the location of the biopsy sample is not known.

Several researchers have sought to simplify the combination of ultrasonography and pathological analysis in the uterine cavity by reducing the number of devices required for insertion in the practice setting. The device (e.g., GOLDSTEIN CATHETER™ manufactured by Cook Medical, Inc of Bloomington, Ind.) can employ a single catheter lumen, a distal opening, a distal shaft with indicia for depth markings, a slideable acorn tip, a proximal coupling used for both the injection of fluid such as saline from the distal end opening, and a vacuum source such as a syringe that will cause fluid and tissue to be withdrawn into the distal opening. In practice, the physician has to simultaneously maintain uterine cavity position and distension with the acorn tip, while manipulating a syringe at the proximal end. In this situation, the physician cannot also operate the ultrasound probe and equipment and would need the assistance of a nurse and technician. In addition, to operate the biopsy mechanism, vacuum needs to be employed within the inner catheter thereby removing all distension and visibility in the uterine cavity. Also, with a vacuum force at the distal end of the catheter, the ability to re-position or re-direct the location of the distal end of the catheter, and what tissue is being collected, is significantly minimized.

In U.S. Pat. No. 8,157,745 to Schoot, which is incorporated by reference herein in its entirety, a method and apparatus is described that combines features of a saline infusion system and a biopsy device that withdraws tissue and fluid within its distal end opening by the withdrawal of an inner mandrel. In Schoot, an acorn tip is fixed to an outer catheter with an inner, slideable, concentric catheter. Within the inner catheter is housed an inner mandrel configured to provide a vacuum force once withdrawn by the physician from at the proximal end. The Shoot system provides a saline source. Using the Schoot device, the physician has to simultaneously maintain uterine cavity position and distension with the acorn tip, while manipulating the withdrawal of the inner mandrel within the inner catheter at the proximal end. In this situation, the physician cannot also operate the ultrasound probe and equipment and would need the assistance of a nurse and technician. In addition, to operate the biopsy mechanism, vacuum is created by withdrawing the inner mandrel and this action removes all distension and visibility in the uterine cavity. Also, with a vacuum force at the distal end of the catheter, the ability to re-position or re-direct the location of the distal end of the catheter, and what tissue is being collected, is significantly minimized.

In practice, it would be beneficial to the physician to have a simplified system that could perform uterine cavity assessments without the need for further technicians, assistants, nurses or manpower, yet maintain a high quality diagnosis. For uterine cavity distension, it would be beneficial if the sealing mechanism of the exocervix was improved. In addition, it would be beneficial if the biopsy system could be easily directed and visualized to allow for a targeted collection of tissue.

SUMMARY OF THE INVENTION

A method of performing a procedure on a uterine cavity of a patient is disclosed. The method can include visualizing the uterine cavity, biopsying a tissue with a biopsy device, and ejecting fluid from the biopsying device into the uterine cavity.

The biopsying can include at least one of advancing, rotating, and withdrawing the biopsy device into the uterine cavity. The biopsy device can have a sealable tip on a repositionable component, proximal indicia and distal indicia. The biopsying device can be configured to biopsy and eject fluid under the control of a single hand of a user of the device.

An apparatus for performing a procedure on a uterine cavity of a patient is also disclosed. The apparatus can have a sealable acorn tip, a handle, a repositioning clip, a distal indicia, a proximal indicia, and a fluid reservoir. The handle can have a pumping lever and a biopsy instrument. The biopsy instrument can be configured to translate and rotate with respect to the handle.

A further apparatus for performing a procedure on a uterine cavity of a patient is disclosed. The apparatus can have an elongated member, a sealable tip, a handle, a repositioning clip, a distal indicial, a proximal indicia, a fluid reservoir; and a vaginal ultrasound probe. The probe can have a rotatable clip attached to at least one of the elongated member and the handle.

DETAILED DESCRIPTION

Figure 1:
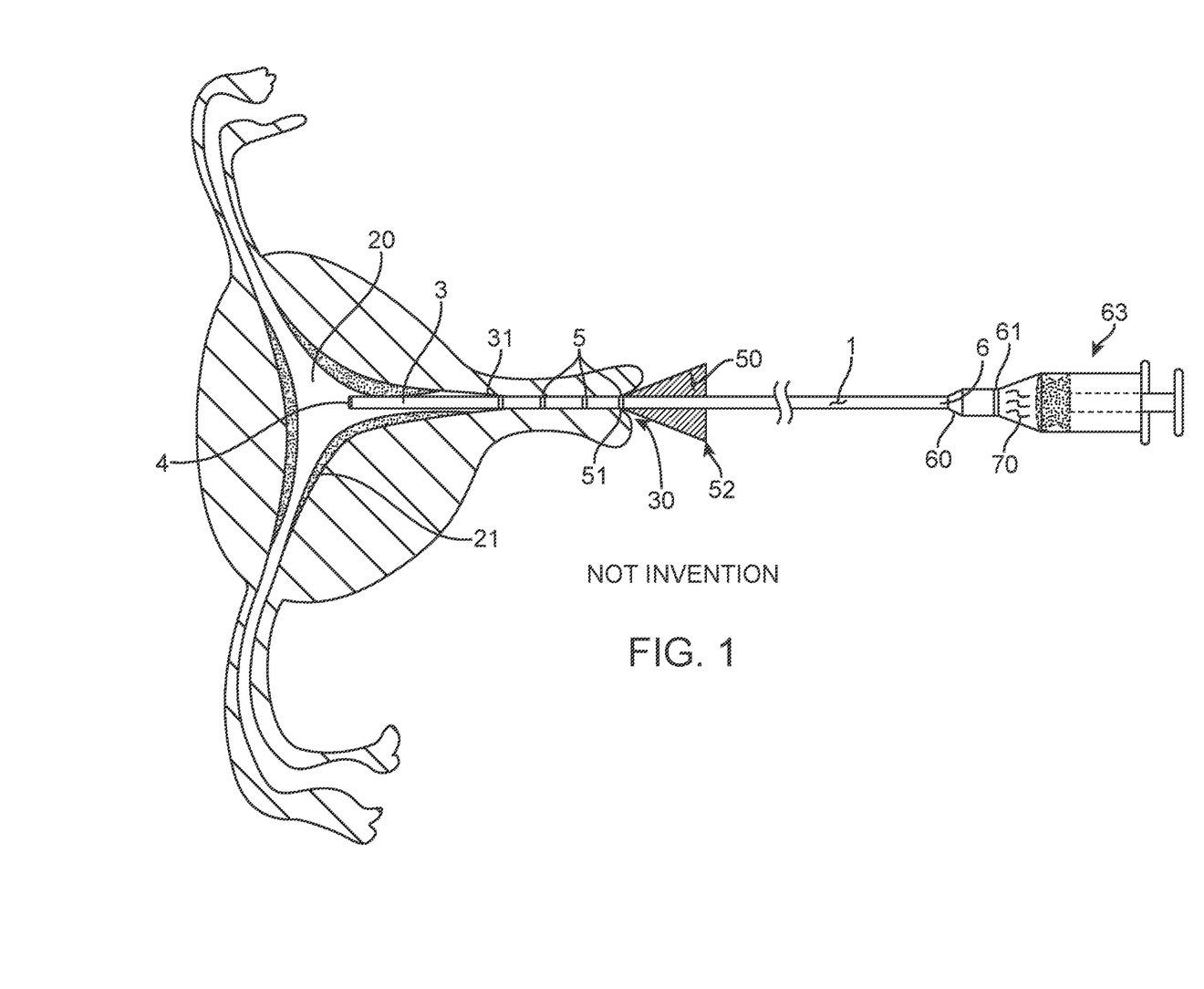
FIG. 1 illustrates one example of a device, not the invention, within the cross-section of a uterine cavity.

In FIG. 1 illustrates a device 1 within a cross-sectional view of the uterine cavity 20. The distal end of the device 3 is shown with a distal end opening 4, inner lumen 6, and indicia 5 for determining the depth of insertion within the uterine cavity using the exocervix 30 of the cervix or endocervical canal 31 as a frame of reference. Located at the exocervical opening 30, an acorn tip 50 is placed and pressed into the exocervical opening 30 to provide a seal for media within the uterine cavity 20. A connector or coupling 60 can be located on the proximal end of the device 1. This coupling 60 can be configured as a stopcock, T-connector or Y-connector to allow for the injection of fluids or media into connector opening 61. This connector opening 61 can be configured as a luer connector to allow for the connection of a syringe 63 or other fluid supplying source. In operation the syringe 63 or other fluid supplying source 64 can be used to distend the uterine cavity 20 when performing an ultrasonographic or radiographic examination of the uterine cavity. Ultrasonography and radiographic equipment are not shown. From connector opening 61, a syringe 63 or other vacuum supplying source can be can be connected to supply negative pressure within the inner lumen 6 of device 1 to withdraw fluid and tissue from the uterine cavity within the distal end opening 4.

The acorn tip 50 can be positioned at the exocervical opening 30. The acorn tip 50 can be configured in a conical shape with smaller diameter distal end 51 and larger diameter proximal end 52. The acorn tip 50 can be slid or re-positioned on distal end of the device 3 to correspond to the desired depth of insertion as indicated by the indicia 5. In practice, a physician may perform a scout film of the uterine cavity 20 by use of the ultrasonographic or radiographic equipment, both not shown in FIG. 1.

The inner lining 21 of the uterine cavity 20 is a potential space. To visualize features, contours and structures within the uterine cavity 20, distension media 70 can be supplied from syringe 63 or other fluid supplying source. The inner most part of the inner lining 21 is the endometrial lining 22 in which this tissue and cells are desired for pathological analysis. Other structures such as polyps, myomas, adhesions, fibroids, septated tissue, and other implantable devices may be located within or protruding into the uterine cavity 20 at the time of examination and their visualization is facilitated by the distension media 70 which separates the potential space (not shown as a potential in these sketches) within the uterine cavity 20.

Figure 2A:
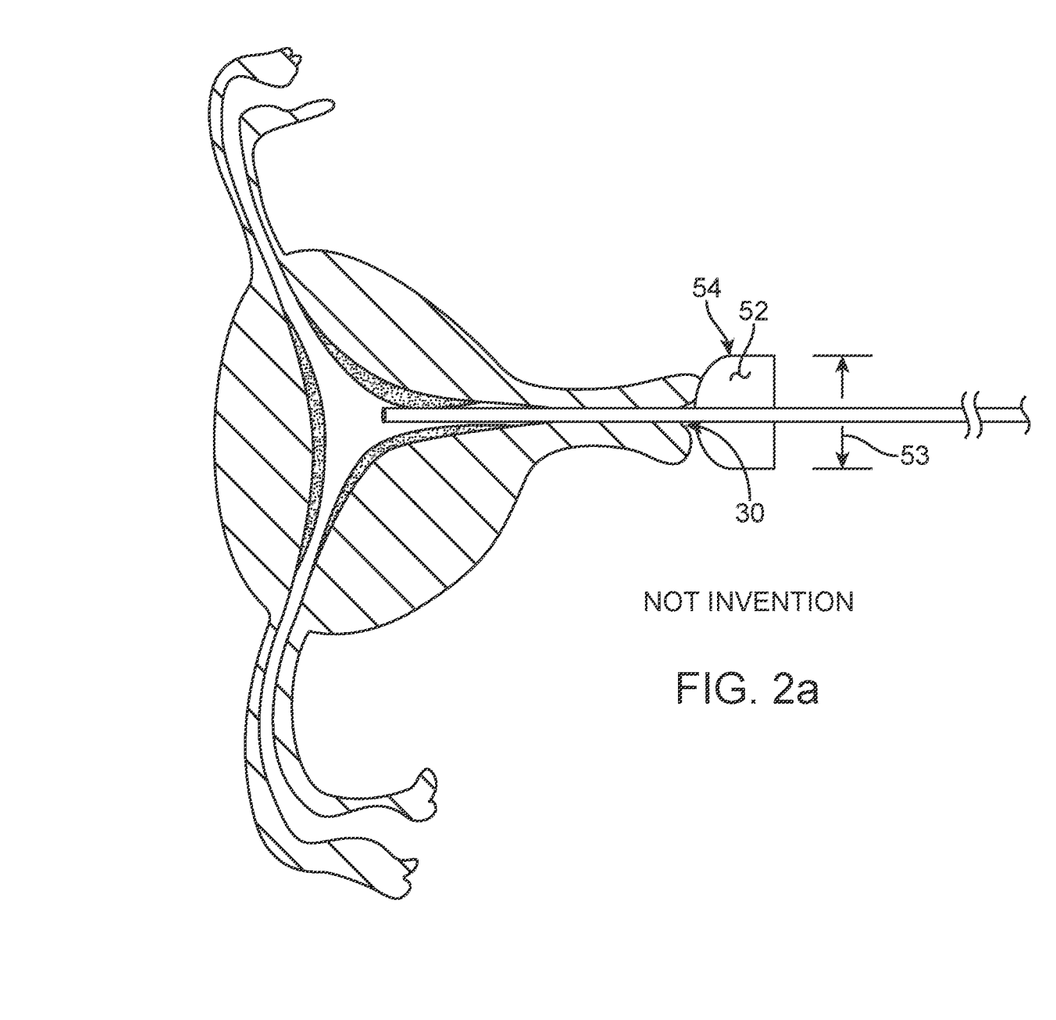
FIGS. 2a, 2b, 2c, and 2d illustrate examples of acorn tips, not the invention, engaging a cross-section view of an exocervix of a patient.

FIGS. 2a, 2b, 2c, and 2d illustrate examples acorn tips 50 or similar devices that can engage the exocervical opening 30 of a patient, shown in cross-section. In FIG. 2a, another acorn tip is depicted as a cylindrical block 52 with outer diameter 53. In practice, the cylindrical block 52 is made of rigid materials such as stainless steel, plastic, or combination of both and is designed to be pressed against the exocervical opening 30. The cylindrical block 52 can have a distal end surface 54 that can be flat, convex, or concave. In FIG. 2a, the cylindrical block is shown with distal end surface 54 drawn as a convex surface.

Figure 2B:
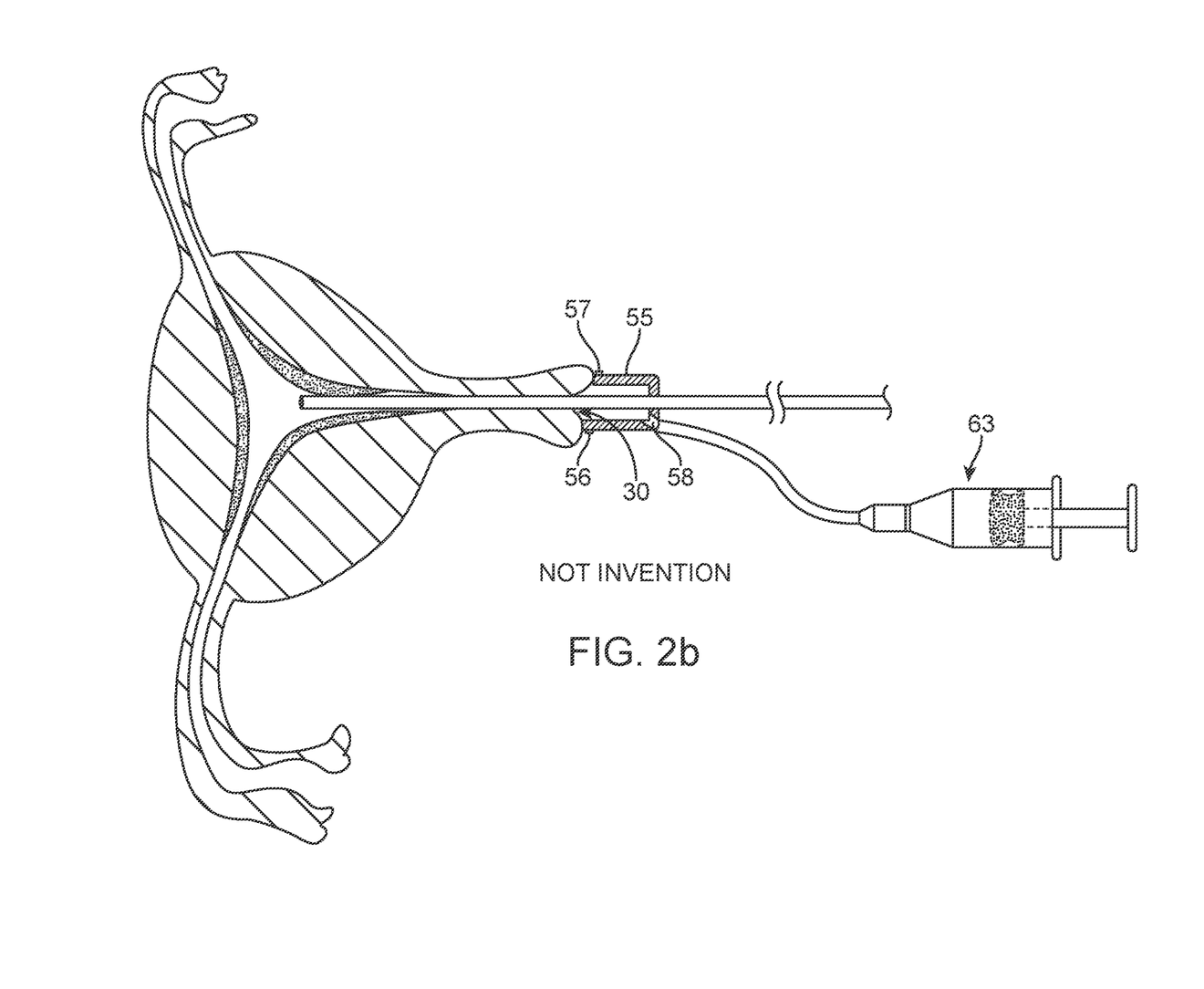

FIG. 2b illustrates a cervical cup 55 which is similar in function to the acorn tip. The cervical cup is designed to engage the exocervical opening with leading edge 57. The area surrounding the exocervical opening 30 is engaged by outer rim 56 of the cervical cup 55. Within the cervical cup 55, a lumen 58 is connected to a syringe 63 or other vacuum supplying source, not shown. By applying vacuum pressure within the cervical cup 55, the outer rim 56 is compressed against the area surrounding the exocervical opening 30 to create a seal.

Figure 2C:
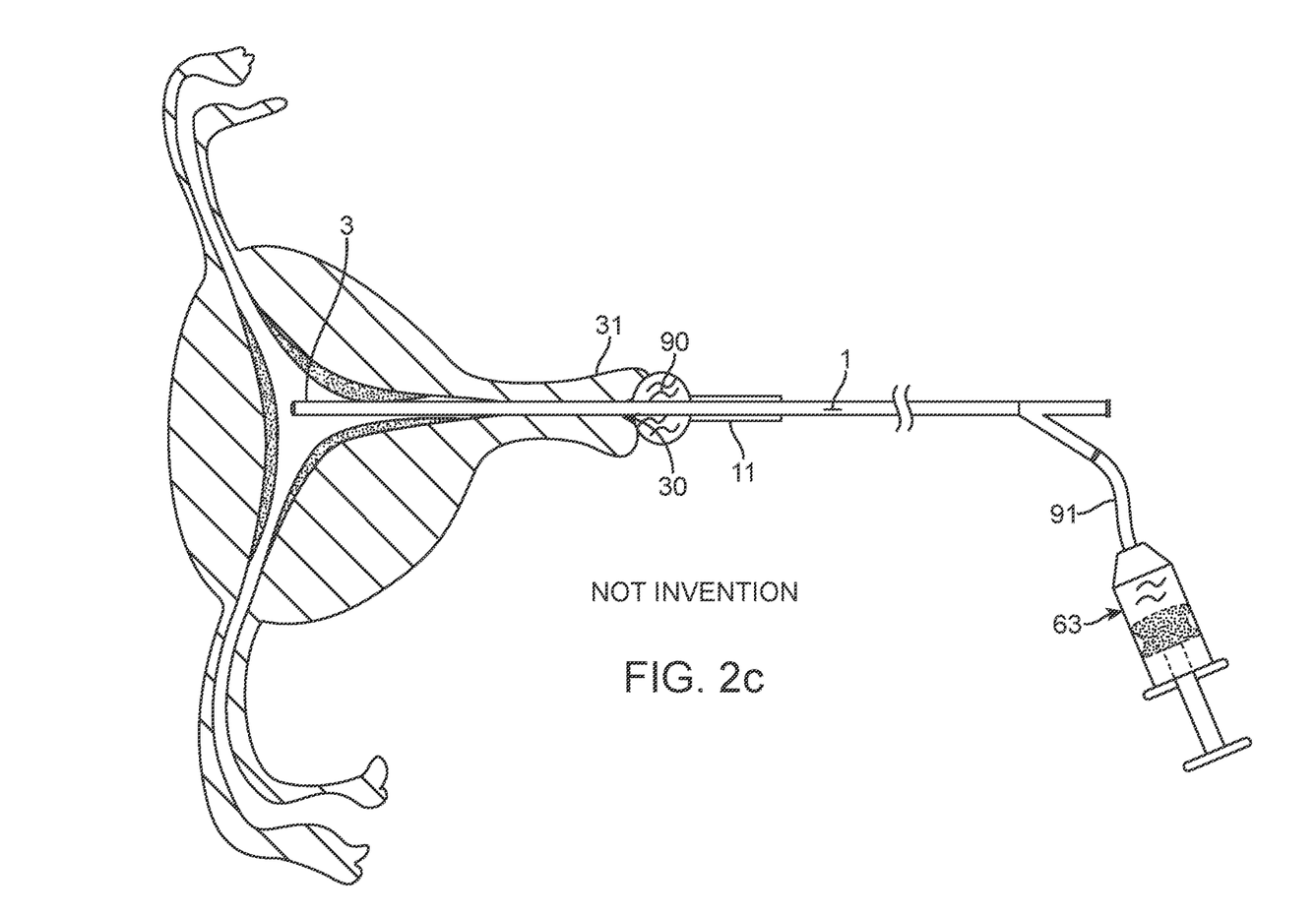

FIG. 2c illustrates a balloon 90 that is placed on the distal end portion 3 of a device 1. The balloon can be inflated by air, gas, fluid, saline, or contrast agent through connection 91 by a syringe 63 or other fluid or air supplying source, not shown. In theory the balloon can be placed on a separate, concentric catheter body 11 so that the insertion depth of the device 1 can be configured appropriately as per the patient's anatomy. In practice, due to the pressure from the air or fluid within the balloon 90, the balloon 90 can back away proximally from the exocervical opening 30 unless stabilizers are employed by a tenaculum, not shown, on the cervix 31.

Figure 2D:
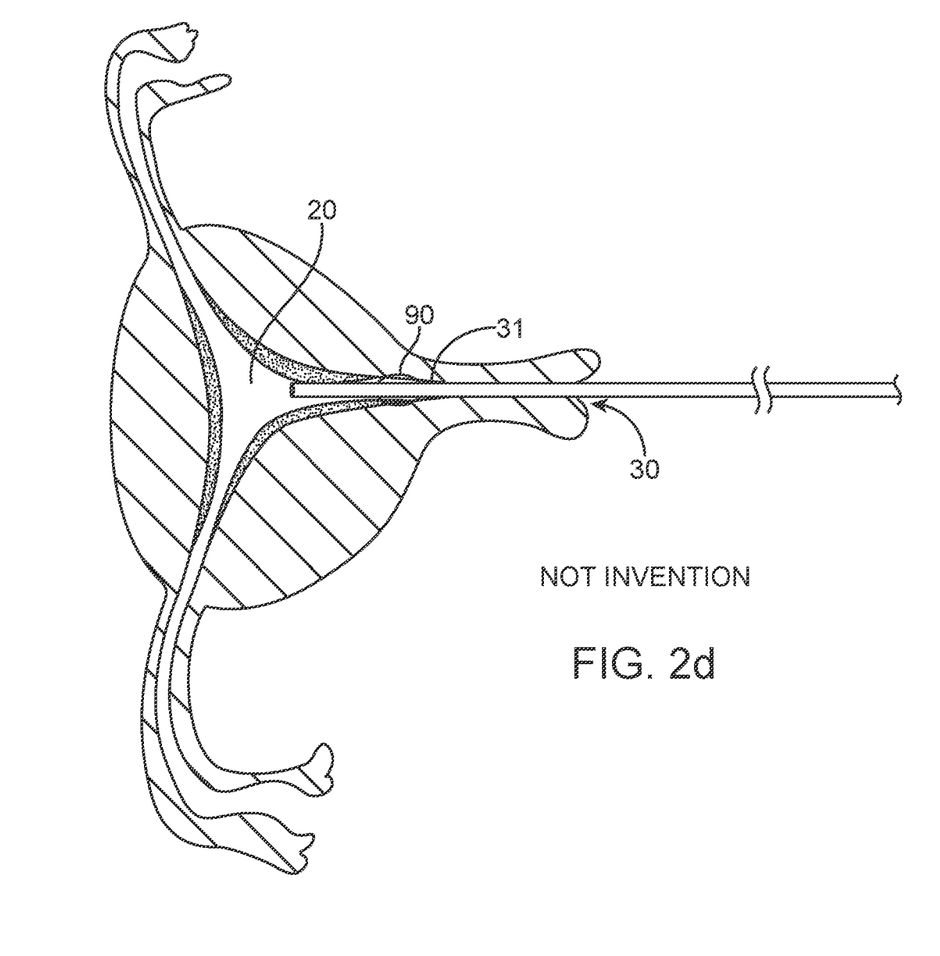

FIG. 2d illustrates another variation of balloon 90 which is inflated within the endocervical canal 31 to create a seal. In this configuration, the air or fluid pressure from the balloon 90 on the endocervical canal can create additional pain and discomfort for the patient. In practice, since the endocervical canal can be irregular in shape, inner diameter, or tortuosity, a balloon 90 can be difficult to stabilize within the cervix 31 without modifications to the balloon surface for greater adhesion to the inner lining of the endocervical canal, or the use of tenaculum stabilizer as described above. Finally, placing the balloon 90 within the uterine cavity 20 at the distal end of the endocervical canal 31 is less desirous since the presence of balloon 90 can obscure anatomical features within uterine cavity 20 during the examination.

Figure 3A:
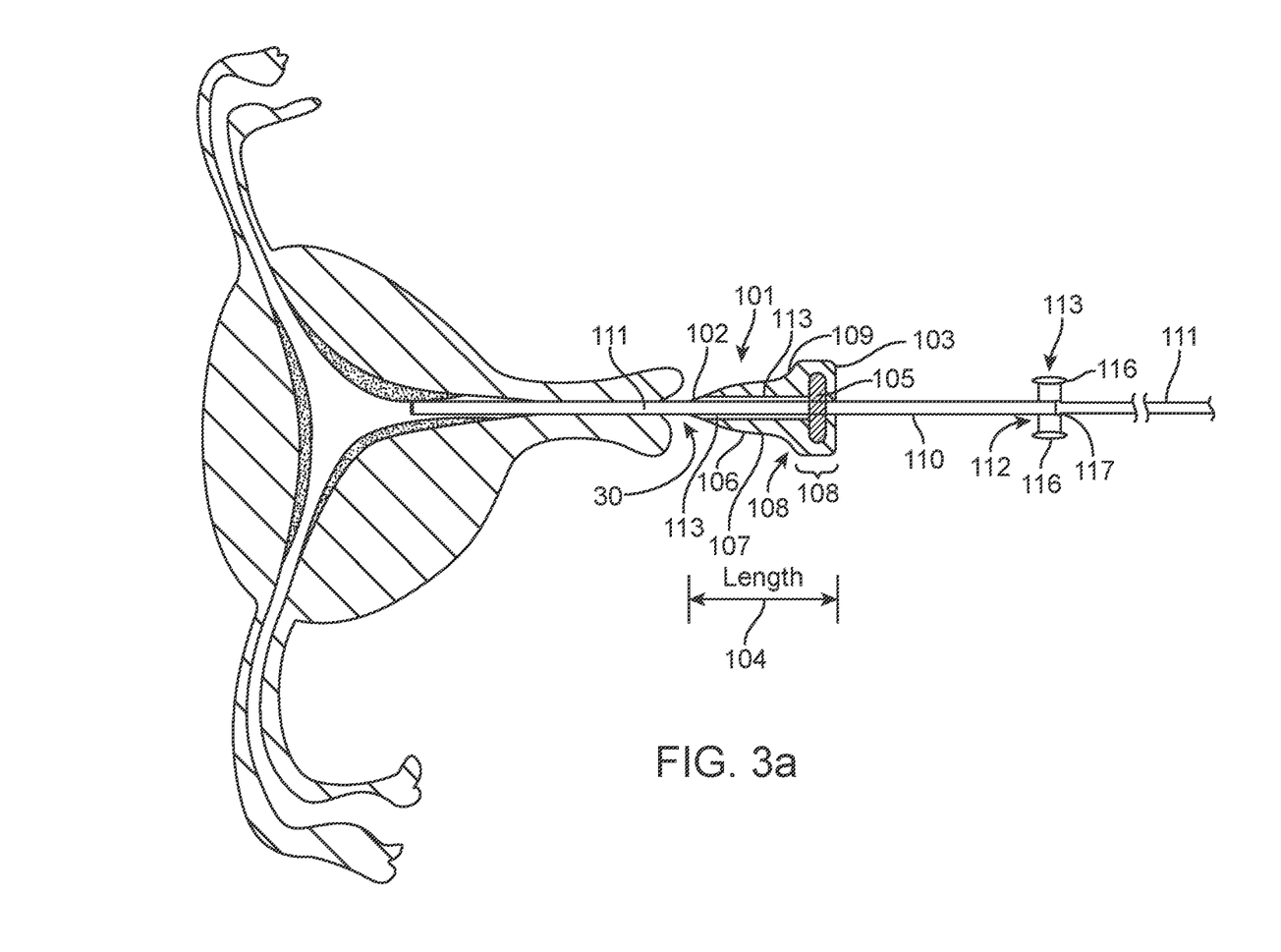
FIGS. 3a and 3b illustrate one configuration of a new sealable acorn tip in a cross-sectional view of a uterine cavity of a patient.

FIG. 3a illustrates one configuration of a new sealable acorn tip 101 about to engage a cross-sectional view of an exocervical opening 30, of a patient. The sealable acorn tip 101 has a smaller distal end 102, in profile, than the proximal end 103 and a length 104. The sealable acorn tip 101 is made from a deformable, resilient material such as silicone. The silicone material can be made from durometers as low as 5 and as high as 60 with 10 to 20 durometer being optimal. Within the sealable acorn tip 101 a separate back plate 105 is placed. Back plate 105 is made from a rigid plastic or metal, and has a diameter or profile less than proximal end 103. The sealable acorn tip 101 can be placed on a translatable or slidable outer catheter 110 that is configured to slide on the distal end portion 3 of device 1. Back plate 105 can be attached to the distal end of outer catheter 110. Back plate 105 can be embedded within sealable acorn tip 101 with pad area 108. Sealable acorn tip 101 can be free floating on outer catheter 110 and can stay attached to back plate 105 through a process of insert molding or other mechanical attachment. Back plate 105 can be affixed to outer catheter 110 or its shaft 111. Thus, areas 113 in FIG. 3a indicate areas without direct adhesion of the sealable acorn tip 101 and outer catheter 110 and shaft 111. Holes and other mechanical features within the back plate 105 create mechanical fixation for the sealable acorn tip 101. The sealable acorn tip 101 can be directly adhered to the back plate 105. In addition, outer catheter 110 and shaft 111 can have a re-positionable clip 112 on the proximal end of area 113.

FIG. 3a also shows sealable acorn tip 101 with leading distal end 102 that is flexible, resilient, and adapted to have a minimal profile for entry into the exocervical opening 30. Just proximal to the distal end 102, a curved, funnel-shaped neck 106 transforms from a concave curve 107 into a larger diameter, convex curve 108 just before the back plate 105 located at the proximal portion of the sealable acorn tip 101. The inflection point 109 can be located at a distance equal to 50%, plus or minus 20%, of the length 104 of the sealable acorn tip 105. By this terminology, an inflection point 109 at 70% would be closer to the proximal end 103 of the sealable acorn tip 101 and would in turn have a longer neck portion 106 and shorter pad area 108. The diameter of the proximal end 103 can be a equal to or larger than 100% larger than the diameter of the distal end 102, or equal to or larger than 200% the diameter of the distal end 102.

Figure 3B:
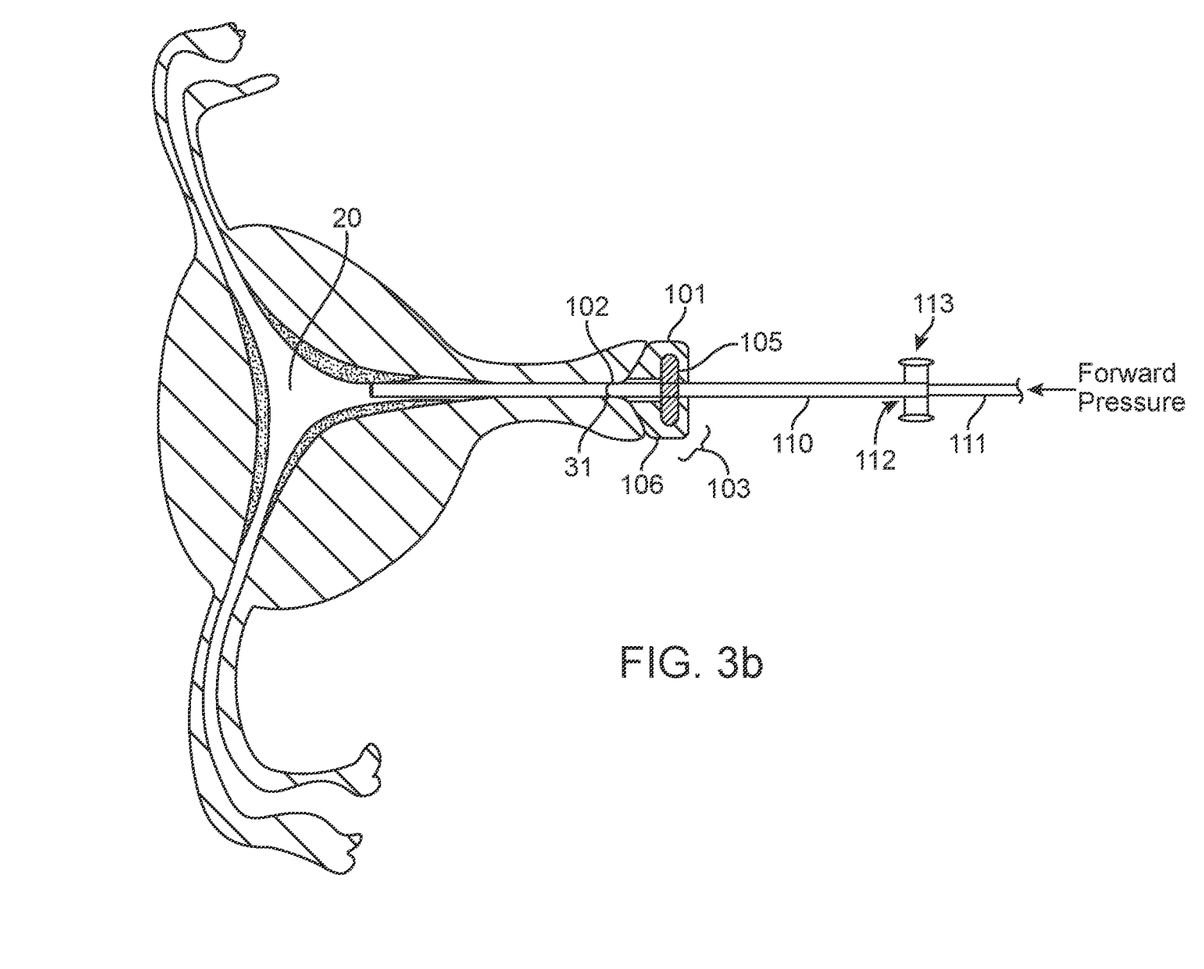

FIG. 3b illustrates the sealable acorn tip 101 in use while forward pressure is being applied by the physician (not shown). The sealable acorn tip 101 provides a sealing element to the endocervical canal 31 to provide distension in the uterine cavity 20 as a result of the free floating aspect and re-formable shape of the sealable acorn tip 101. As the physician provides forward pressure on the device, the back plate 105 and re-forms the sealable acorn tip 101 by providing a re-forming surface from within the sealable acorn tip 101. The distal end 102 intubates the exocervical canal and the bulging proximal end 103, which expands in outer diameter in response to the forward pressure, serves to occlude the endocervical canal 31. Also in response to forward pressure, neck portion 106 expands in outer diameter and depending upon the patient anatomy and the forward pressure applied by the physician, the entire length of the sealable acorn tip can compress up to 50%. In FIG. 3b, distal surface of back plate 105 is illustrated as a flat surface but the distal surface may be convex, conical, or contain multiple projections to provide further re-forming force to the sealable acorn tip 101.

The sealable acorn tip 101 can be resilient and translucent, for example, so the physician has visibility of the approaching cervix as the device is being inserted. The sealable acorn tip can have an illumination element or LED (not shown) that can provide additional light within the vagina. Illumination can be provided in a co-axial fashion as an added component to the outer catheter shaft 110, illumination not shown.

The sealable acorn tip 101 can be applied to a number of devices and sheaths that are used in uterine cavity assessment without biopsy including diagnostic and operative hysteroscopy, hysterosalpingography, SIS, and intrauterine insemination.

FIG. 3a illustrates that re-positionable clip 112 can be located the proximal end 113 of outer catheter 110, for example, to provide a pre-determined insertion depth for the device within the uterine cavity 20. Re-positionable clip 112 can have two configurations. In the normal or resting state, the re-positionable clip 112 can provide a fixation force with holding grips 117 for outer catheter 110 on distal end portion 113 of a device. When outer tabs 116 of the re-positionable clip 112 are compressed, holding grips 117 can be released or open to remove the fixation force. Thus the re-positionable clip 112 can have a resilient force in the closed position to hold the repositionable clip 112 on the device. The re-positionable clip can be configured to close upon the compression force supplied by the physician and open upon a releasing force by the physician.

Figure 4A:
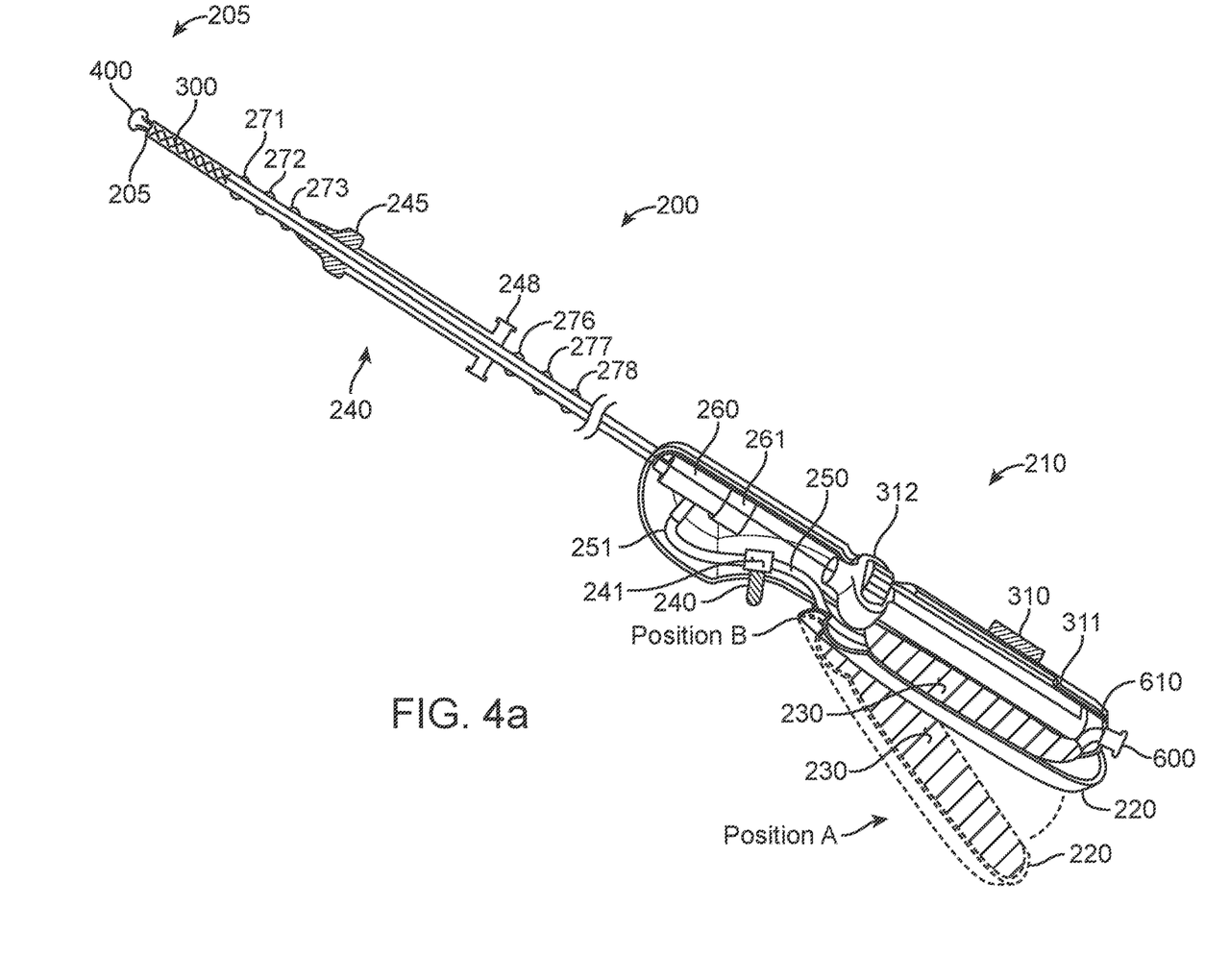
FIGS. 4a and 4b illustrate one configuration of a device for performing simultaneous sonography and biopsy with partial cross sectional views.
Figure 4B:
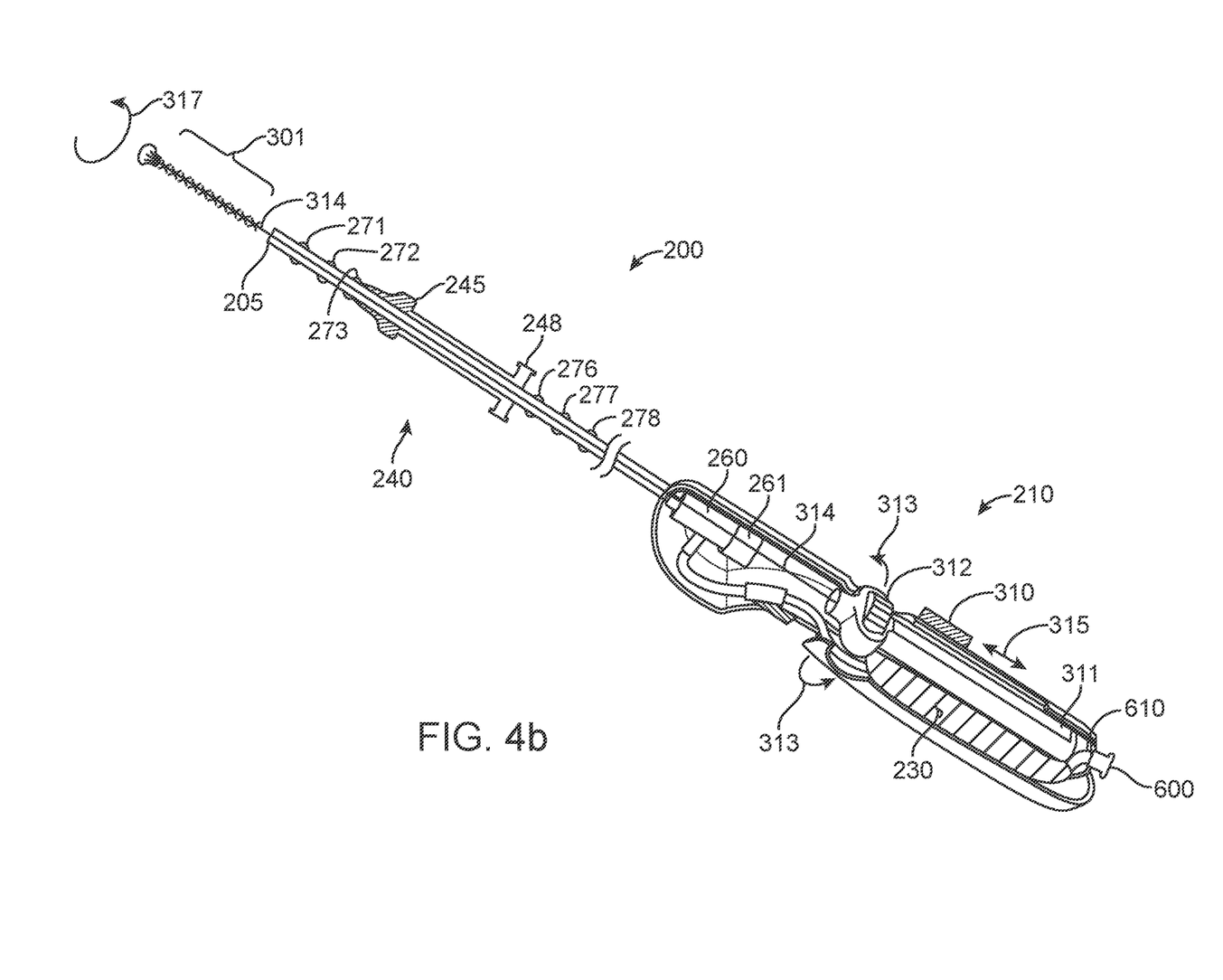

FIG. 4 illustrates one configuration of an apparatus for performing simultaneous, concurrent, or concomitant sonography and biopsy. At the proximal end of device 200, there is a handle 210, which is shown in partial cross section. The handle 210 can be grasped by the physician with one hand. Within handle 210, there can be a lever 220 shown in two positions. In Position A, the lever can have a fluid bag 230 that can contain saline, contrast agent, therapeutic agent such as lidocaine, or other solution that enables visualization by ultrasonography or radiography, or combinations thereof. In Position B indicated in the drawing, the lever 220 can be depressed closer to handle 210 which forces the fluid in bag 230 to be ejected from the device 200 at its distal end 205. Lever 220 facilitates the delivery of fluid from bag 230 since the physician does not need to move or withdraw his or her hand to force the action to occur. Prior to ejecting the fluid, and near the index finger of the physician, there can be a lever or trigger 240 that can be actuated by the physician prior to ejecting the fluid. Trigger 240 can be a gate valve, stop cock, or pinch valve but can be positioned and actuated without requiring the physician to use another hand, or change hand position, on handle 210. Actuating the trigger 240 opens the conduit 250 pass the valve 241 and through conduit 251. From there fluid flows through T-connector 260 with o-ring seal at its proximal end 261. The o-ring seal (not shown) allows for a biopsy instrument 300 to translate and rotate through T-connector 260 without a loss of fluid or leak at the proximal end 261.

Alternatively, trigger 240 mechanism can be a check valve (not shown) that can remain in the closed condition or state until the physician squeezes the fluid bag 230 with enough force to open the cracking pressure of the check valve. Such cracking pressure can be 1 to 2 psi or greater.

Handle 210 can contain a mechanism for advancing, rotating, and retracting a biopsy instrument 300 contained within the central lumen of device 200. Advancement and retraction of the biopsy instrument 300 can be done by pushing button 310 forward or backward on track 311. The position of button 300 can be placed to allow a one-handed approach to actuating the biopsy instrument 300 without requiring the physician to move or alter his or her hand position throughout the entire procedure. In practice, the biopsy instrument 300 can be advanced forward along track 311 in the translational direction indicated by motion 315. Once advanced, the biopsy component 301, shown as biopsy bristles or brushes, can be positioned inside the uterine cavity (not shown) and beyond the distal end 205 of device 200. Other biopsy components are feasible including ridges, mechanical shavers, or graspers (not shown). Moreover once advanced from the distal end 205 of device 200, turn knob 312 is provided on handle 210 that can be easily rotated, as indicated by motion 313. The motion 313 serves to rotate the central core 314 of the biopsy instrument 300 and thereby rotates the biopsy components 301 in the motion 317 indicated. Once rotated inside the uterine cavity (not shown), the biopsy instrument 300 is withdrawn back into the distal end 205 of device 200 by retracting the button 310 back along track 311.

Outer catheter 240 can be at the mid-section of device 200. Outer catheter 240 can contain a reposition clip 248 at its proximal end and a sealable acorn tip 245 at its distal end. FIG. 4a depicts the sealable acorn tip 245 in a state prior to intubation within the exocervix of a patient (not shown). FIG. 4b depicts the sealable acorn tip 245 in a state in which the physician has placed the device 200 under a compressive force against the exocervix (not shown) in which the sealable acorn tip is depicted with bulging proximal end as a result of the back plate pushing the proximal pad and neck as a result of the free floating attachment of the sealable acorn tip 245 that was described earlier.

As described earlier, re-positionable clip 248 can be placed in a state that locks outer catheter 240 to the device. The location of the re-positionable clip 248 can be placed to allow the physician to lock the location of the sealable acorn tip 245 outside of the vagina. To facilitate the re-positioning performed by the physician, two sets of indicia can be provided. Distal indicia indicated by 271, 272, and 273 in FIGS. 4a and 4b. More or less distal indicia that provide a frame of reference for depth of insertion are possible. Distal indicia 271, 272, and 273 indicate the depth of insertion of distal end 205 within the uterine cavity (not shown). Proximal indicia, 276, 277, and 278 can provide a visual reference for the physician while the device 200 is inserted inside the patient. Proximal indicia 276, 277, and 278 can remain outside of the vagina as a result of its location on device 200 and the length of outer catheter 240. The device can have more or less proximal indicia that can provide an external frame of reference for the physician.

Biopsy instrument 300 can have a bulbous, rounded, tear-drop shaped, or ball tip 400 at its distal end at the distal end 205 of device 200. The ball tip 400 can provide a less traumatic leading surface of device 200, when the biopsy instrument 300 is retracted within the distal end 205 of the device 200, and for the biopsy instrument 300 when the biopsy instrument 300 is advanced beyond the distal end 205 when a biopsy is taken. The proximal hemi-spherical section of ball tip 300 can have fenestrations, grooves, or channels so that fluid from bag 230 can be easily ejected from distal end 205 when the ball tip 400 is fully retracted within distal end 205.

FIG. 4a illustrates a handle 210 that can eject fluid from bag 230 by the actuation of a lever 220 by pumping action that takes lever 220 from Position A to Position B in a one handed technique. There are several alternatives for this action including the introduction of air or gas pressure with a CO2 cartridge or pumping air pressure within the bag system through a separate check valve (not shown). In addition, the fluid bag could be positioned in a foot pedal system in which the physician can eject fluid by depressing a foot actuated system (not shown). Other pump systems or gravity feed systems are possible.

In FIGS. 4a and 4b, fluid bag 230 can be supplied prefilled to the physician. In addition, at the proximal end of handle 210, or anywhere on handle 210, a luer connector 600 is placed with conduit 610 connected to fluid bag 230. With luer connector 600 and conduit 610, the physician can add different or additional fluid media or agents to fluid bag 230, for example when media is desired for further diagnostic information, or if a new fluid agent, such as a gel or foam, was desired for added visualization or the application of a therapeutic agent, such as lidocaine, is desired during a procedure.

In addition, the advancement or button 310 and subsequent rotation of turn knob 312 can be controlled by a motor (not shown). The addition of the motor would continue the desire to keep a one-handed procedure without additional manipulations for the physician. There would be cost benefits by not having a motor as depicted in FIGS. 4a and 4b.

Figure 5A:
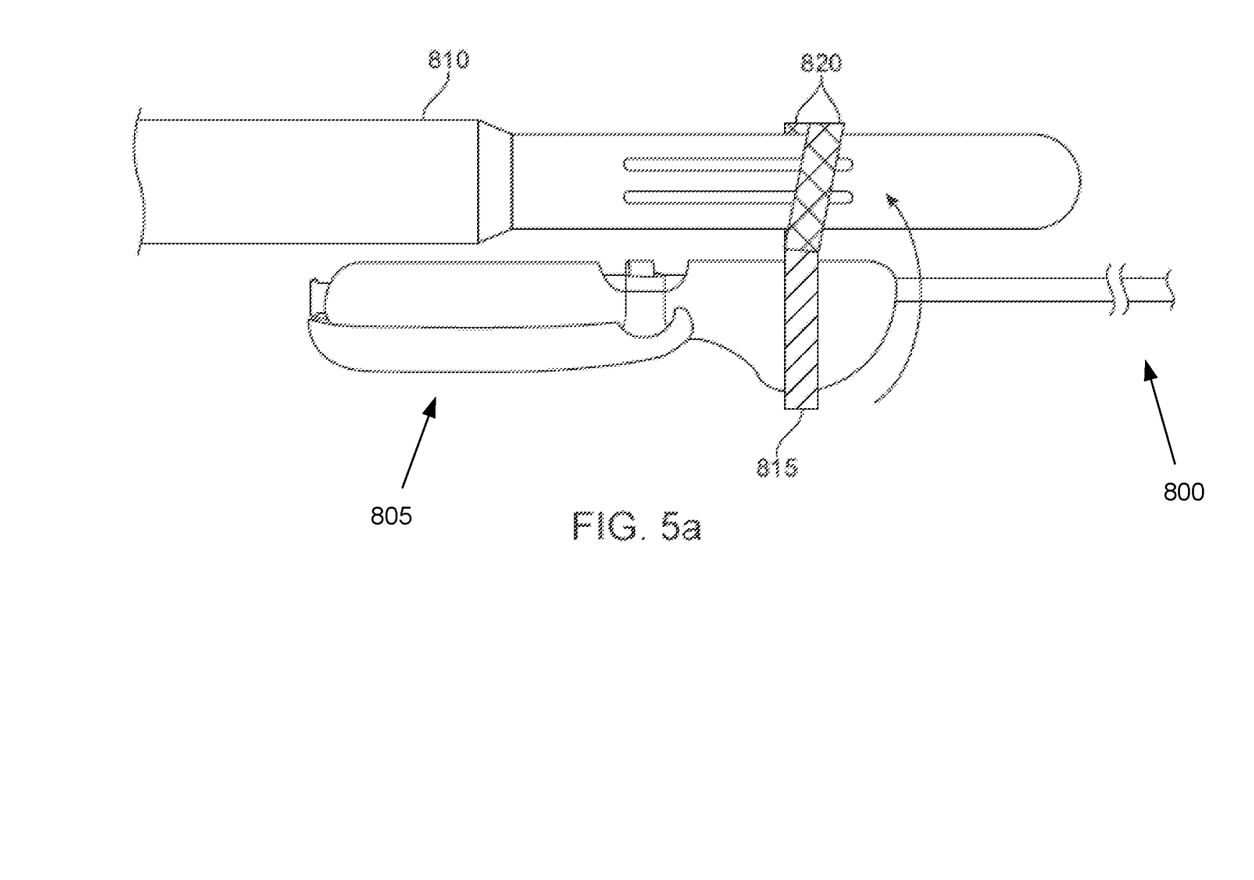
FIGS. 5a and 5b illustrate one configuration of an apparatus for performing simultaneous sonography and biopsy that engages a vaginal ultrasound probe during a uterine cavity assessment.
Figure 5B:
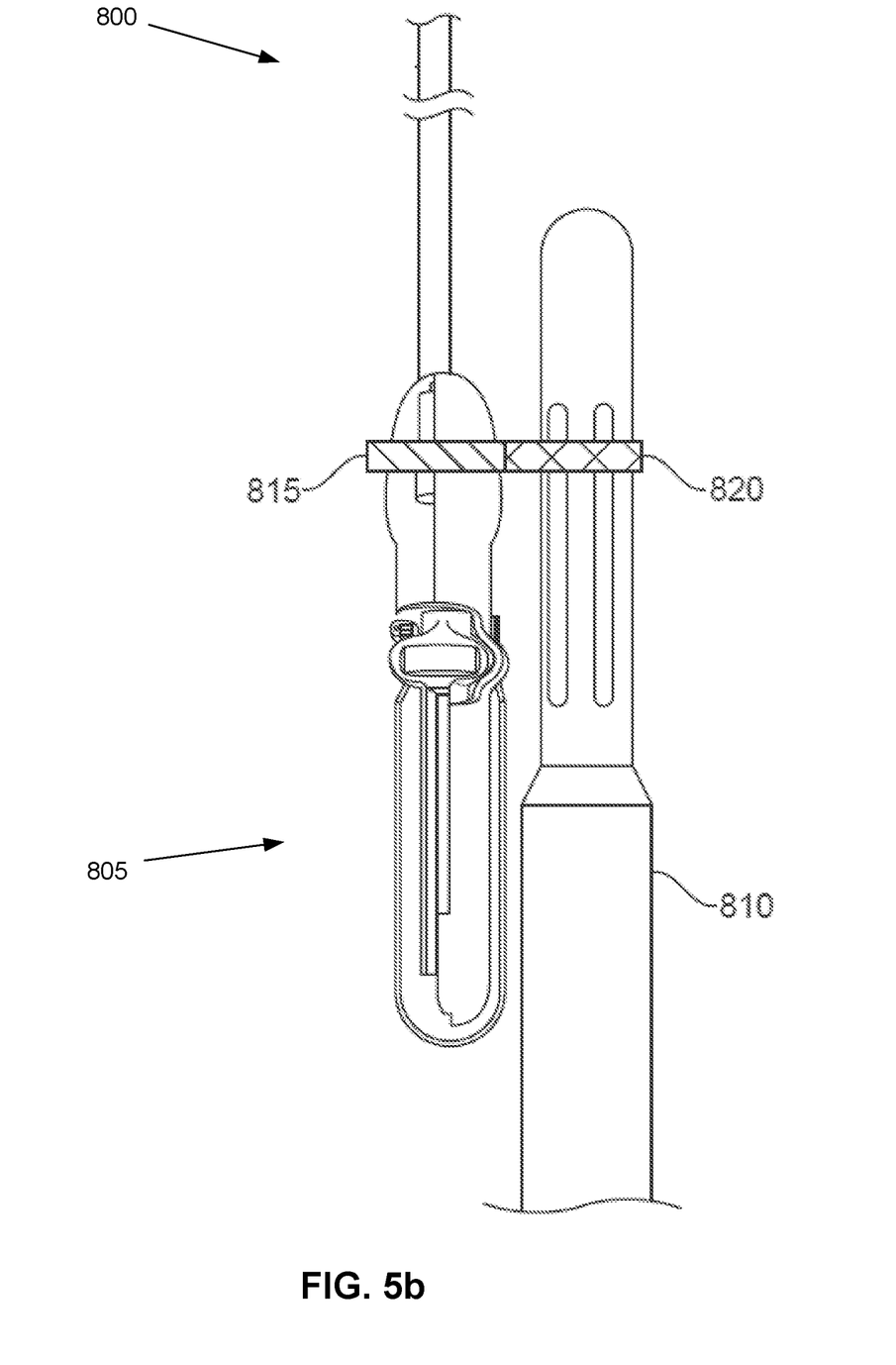

FIGS. 5a and 5b illustrate one configuration of an apparatus for performing simultaneous sonography and biopsy that engages a vaginal ultrasound probe 810 during a uterine cavity assessment (uterine cavity not shown). During a procedure, gynecologists will typically use a vaginal ultrasound probe for performing a diagnostic assessment. In practice, this requires one hand of the physician to be on the vaginal ultrasound probe 810 while the other hand would be needed to remain on the handle 805 of device 800. One mechanism to make this process easier for the physician is illustrated in FIG. 5a with handle 805 in side view, and FIG. 5b with handle 805 in top view. In both FIGS. 5a and 5b, rotatable, repositionable, clip 815 is located on the distal portion of handle 805. Clip 815 contains arm projections 820 that are configured to grasp and lock onto vaginal ultrasound probe 810. Arm projections 820 can contain indentations, grips, mechanical locks, magnets, Velcro, or straps to maintain position of the vaginal ultrasound probe 810 with handle 805.

An apparatus and method for performing simultaneous ultrasonography, or radiographic visualization, and biopsy without loss of visualization during the biopsy step is disclosed herein. The apparatus is configured to perform both procedures with one instrument and one hand position by the physician. The one hand position can allow the physician to use his or her free hand to stabilize the patient, operate ultrasound controls, or manipulate another device or instrument without the requirement of additional manpower. Being able to perform both procedures with only one device insertion can reduce procedure time and cost for the physician, patient, and payors.

The sealable acorn tip and outer catheter configuration with re-positionable clip can be a separate device for mounting onto traditional hysteroscopy sheaths and other devices utilized in uterine cavity procedures.

The system described herein could be utilized as a platform for the introduction of other materials and therapeutic agents into the uterine cavity such as gels, foams, and contrast agents for either echogenicity or radiographic visualization. Other therapeutic agents can be applied through this platform including sclerosing, contraception, and adhesion prevention agents. Additional agents can include gametes, blastocysts, and other biological products utilized in infertility procedures.

The biopsy instrument described herein could be replaced or removed before or after use by another instrument such as a polypectomy snare (with or without a coupling to an electrosurgical energy source), biopsy cup, grasper, probe, endoscope, drug or energy delivery device, or other instrument for a therapeutic or diagnostic procedure. The biopsy instrument can be replaced by an implant delivery device that provides permanent contraception within the fallopian tube or uterine cavity.

The physician can locate the biopsy instrument at a targeted region within the body cavity, for example by using ultrasonography or radiographic visualization simultaneously with a biopsy procedure. For gynecologic practice, physicians may want to target certain regions of the uterus if atypical lesions or identified with diagnostic visualization. Utilizing a biopsy instrument that does not require vacuum pressure to withdraw tissue within the distal end of the device allows for both of these procedures to be performed simultaneously. Coupled with the use of a sealable acorn tip that reforms within the endocervical canal at the exocervix this procedure can reduce the amount of manpower, steps, or hands required to perform the procedure. This is especially true since endocervical canals are presented to the physician in a multitude of shapes and configurations. They are not round and cylindrical but instead in majority they are elliptical, irregular, and unpredictable in shape and configuration.

In describing the method of performing simultaneous ultrasonography, or radiographic examination, and biopsy, the physician would prepare the vagina and cervix as per standard technique. Typically the physician would take a scout film or ultrasound view to distinguish anatomical landmarks. In some cases, the length of the cervical canal and uterine cavity would be determined. Alternatively, the physician may sound or measure the length of the uterine cavity by retracting the sealable acorn tip to its most proximal position prior to insertion through the cervix and into the uterine cavity. If the length of the cervix and uterine cavity is determined, and a depth of insertion into the uterine cavity is calculated, the physician could then set the re-positionable clip on the device to the desired length using the indicia provided on the device. The device could be inserted into the cervix until the sealable acorn tip engages the exocervix with slight forward pressure. The bulging of the proximal pad area of the sealable acorn tip can be visualized and felt with tactile sensation. The trigger on the handle of the device can then be released to open the conduit of the fluid bag to the distal end of the device.

Alternatively, the physician may eject fluid out of the distal end of the device while inserting the device through the cervix to create a hydraulic distending action through the endocervical canal and uterine cavity. Once positioned in the uterine cavity with the sealable acorn tip engaged and reformed into place at the exocervix, the physician can then pump additional fluid, such as saline, into the uterine cavity to distend the cavity and create room for visualization. Additional fluid may be placed into the cavity for assessing patency in the fallopian tubes and viewing other anatomical features. Additional fluid can be inserted into the proximal luer connector and conduit that facilitates the addition of extra fluid during a procedure. The fluid bag can be pre-filled with an appropriate amount of fluid at the start of a procedure. The physician can change the depth of insertion of the device by opening and repositioning the clip if necessary by utilizing the proximal indicia, which is visible outside of the vagina, to re-position the distal end of the device. The physician may wish to target the distal end of the device at or near a region of interest inside the uterine cavity. The physician can advance the button on the handle to advance the biopsy instrument towards the region of interest. The rotatable turn knob allows the physician to rotate and manipulate the biopsy components in a fashion to collect, cut, grasp, or shave the tissue of interest. Once done, the physician can retract the button on the handle to retract the biopsy instrument within the distal end of the device. Then the physician can withdraw the entire device from the patient. Once outside of the patient, the physician can place the distal of the device into a specimen container and re-advance the biopsy instrument within the specimen container. The physician may elect to advance and retract the biopsy instrument several times against the distal end of the device to further release tissue contents collected on the biopsy components.

Materials and manufacturing techniques may be employed as within the level of those with skill in the relevant art. The same may hold true with respect to method-based aspects of the disclosure in terms of additional acts commonly or logically employed. Any optional feature of the variations described herein may be set forth and claimed independently, or in combination with any one or more of the features described herein. Reference to a singular item includes the possibility that there are plural of the same items present. More specifically, as used herein, the singular forms "a," "and," "said," and "the" include plural referents unless the context clearly dictates otherwise. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art. The breadth of the present disclosure is not to be limited by the subject specification, but rather only by the plain meaning of the terms employed.

All publications and patent applications mentioned in this specification are herein incorporated by reference to the same extent as if each individual publication or patent application was specifically and individually indicated to be incorporated by reference.

We claim:

1. An apparatus for performing a procedure on a uterine cavity of a patient comprising:
an elongated member having a distal port, and wherein the distal port is controllably obstructable by structure of the apparatus when the distal port is in the uterine cavity;
a sealable acorn tip attached to the elongated member;
a handle comprising a pumping lever, wherein the handle has a handle longitudinal axis, wherein the pumping lever is configured to rotate around a pivot, and wherein the pumping lever has a pumping lever longitudinal axis, and wherein when the pumping lever is in a first configuration, the pumping lever longitudinal axis is parallel with the handle longitudinal axis;
a biopsy instrument, and wherein the biopsy instrument is configured to translate with respect to the elongated member and rotate with respect to the handle;
a repositioning clip on the handle-side of the acorn tip;
a distal indicia along the elongated member;
a proximal indicia along the elongated member; and
a fluid reservoir mechanically connected with the pumping lever, and wherein the fluid reservoir comprises a refillable fluid bag;
wherein the biopsy instrument is configured to extend out of and retract into the elongated member.

2. The apparatus of claim 1, wherein the tip comprises a rigid plate.

3. The apparatus of claim 1, further comprising a rigid plate embedded in the tip.

4. The apparatus of claim 1, wherein the biopsy instrument is configured to advance with respect to a remainder of the handle.

5. The apparatus of claim 1, wherein the biopsy instrument is configured to withdraw with respect to a remainder of the handle.

6. The apparatus of claim 1, wherein the fluid reservoir is in a compressed state when the handle is in the first configuration.

7. The apparatus of claim 1, wherein the handle further comprises a controller on a surface of the handle opposite the pumping lever.

8. The apparatus of claim 7, wherein the controller is configured to allow one-handed operation of the apparatus throughout an entire procedure.

9. The apparatus of claim 1, wherein the distal port is controllably obstructable by the biopsy instrument when the distal port is in the uterine cavity.

10. An apparatus for performing a procedure on a uterine cavity of a patient comprising:
an elongated member having a distal port, wherein the distal port is controllably obstructable by structure of the apparatus when the distal port is in the uterine cavity;
a sealable tip attached to the elongated member;
a handle comprising a pumping lever configured to rotate around a pivot, wherein the handle has a handle longitudinal axis, and wherein the pumping lever has a pumping lever longitudinal axis, and wherein when the pumping lever is in a first configuration, the pumping lever longitudinal axis is parallel with the handle longitudinal axis;
a repositioning clip on the handle-side of the sealable tip of the elongated member;
a distal indicia along the elongated member;
a proximal indicia along the elongated member;
a fluid reservoir mechanically connected to the pumping lever, wherein the fluid reservoir comprises a refillable fluid bag;

a vaginal ultrasound probe comprising a rotatable clip attached to at least one of the elongated member and the handle; and a biopsy device configured to extend out of and retract into the elongated member.

11. The apparatus of claim 10, wherein the tip is acorn-shaped.

12. The apparatus of claim 10, wherein the tip comprises a rigid plate.

13. The apparatus of claim 10, further comprising a rigid plate embedded in the tip.

14. The apparatus of claim 10, wherein the rotatable clip is configured to be translatable along at least one of the elongated member and the handle.

15. An apparatus for performing a procedure on a uterine cavity of a patient comprising:

a handle comprising a pumping lever, wherein the pumping lever is configured to rotate around a pivot, and wherein the handle has a handle longitudinal axis, and wherein the pumping lever has a pumping lever longitudinal axis, and wherein when the pumping lever is in a first configuration, the pumping lever longitudinal axis is parallel with the handle longitudinal axis;

an elongated member extending from the handle; wherein the elongated member has a distal port, and wherein the distal port is controllably obstructable by a biopsy instrument when the distal port is in the uterine cavity, wherein the biopsy instrument is configured to translate with respect to the elongated member and rotate with respect to the handle;

a sealable tip along the elongated member; and a fluid reservoir comprising a refillable bag, wherein the fluid reservoir is attached to at least one of the handle or pumping lever;

wherein the biopsy instrument is configured to extend out of and retract into the elongated member.

16. The apparatus of claim 15, wherein the tip comprises a rigid plate.

17. The apparatus of claim 15, further comprising a vaginal ultrasound probe comprising a rotatable clip attached to at least one of the elongated member and the handle.

18. The apparatus of claim 17, wherein the rotatable clip is configured to be translatable along at least one of the elongated member and the handle.

* * * * *